United States Patent [19]

Schlegel et al.

[11] Patent Number: 4,978,774
[45] Date of Patent: Dec. 18, 1990

[54] PROCESS FOR THE PREPARATION OF D(+)-2-(4-ACETYLPHENOXY)-PROPIONIC ESTERS

[75] Inventors: Günter Schlegel, Liederbach; Hilmar Mildenberger, Kelkheim, both of Fed. Rep. of Germany

[73] Assignee: Hoechst Aktiengesellschaft, Frankfurt am Main, Fed. Rep. of Germany

[21] Appl. No.: 470,101

[22] Filed: Jan. 25, 1990

[30] Foreign Application Priority Data

Jan. 27, 1989 [DE]  Fed. Rep. of Germany ....... 3902372

[51] Int. Cl.$^5$ .............................................. C07C 69/76
[52] U.S. Cl. ..................................................... 560/53
[58] Field of Search .......................................... 560/53

[56] References Cited

U.S. PATENT DOCUMENTS 4,130,413 12/1978 Handte et al. ........................ 71/90
4,531,969  7/1985 Nestler et al. ....................... 71/108

FOREIGN PATENT DOCUMENTS 0002800 12/1978 European Pat. Off. .
302786  3/1989 European Pat. Off. .
302787  3/1989 European Pat. Off. .
334595  9/1989 European Pat. Off. .
334596  9/1989 European Pat. Off. .
2640730  3/1978 Fed. Rep. of Germany .
62-178543  5/1987 Japan .
307837 12/1988 Japan .

*Primary Examiner*—Paul J. Killos
*Attorney, Agent, or Firm*—Curtis, Morris & Safford

[57] ABSTRACT

Process for the preparation of D(+)-2-(4-acetylphenoxy)-propionic esters

Preparation of D(+)-2-(4-acetylphenoxy)-propionic esters of the formula

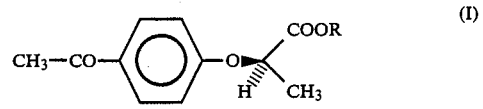

by reacting 4-hydroxyacetophenone with L-halo- or sulfonyloxy-lactic esters in a basic medium at temperatures $\leq 50°$ C.

13 Claims, No Drawings

PROCESS FOR THE PREPARATION OF D(+)-2-(4-ACETYLPHENOXY)-PROPIONIC ESTERS

Optically active 2-(4-acetylphenoxy)-propionic esters are valuable precursors for the preparation of 2-(4-hydroxyphenoxy)propionic acid derivatives which, in turn, are used as starting compounds for herbicidal (hetero)aryloxyphenoxypropionic acid derivatives, for example for the preparation of fenoxaprop-ethyl; see DE-A 2,640,730 (U.S. Pat. No. 4,130,413) and EP-A 2,800 (U.S. Pat. No. 4,531,969). The title compounds are known from JP-A 62/178,543. The process quoted therein (reaction of 4-hydroxyacetophenone with L-lactic ester) is preferably carried out at 80°–100° C. In this process, however, the D-enantiomer of the phenoxypropionate, which is formed, is racemized to a considerable extent. In the further reaction, this would entail the formation of herbicidally inactive L-(hetero)aryloxyphenoxypropionic acid derivatives. Since it is desirable for economical and ecological reasons to employ the herbicidal active substance as enantiomerically pure as possible, the L-component must be separated from the precursor, which is only possible with a complicated procedure.

Surprisingly, it has now been found that the formation of the undesirable L-enantiomer is nearly totally suppressed when the reaction described in JP-A 62/178,543 is carried out at reaction temperatures of not more than 50° C., i.e., far below the preferred range indicated.

Thus, the invention relates to a process for the preparation of D(+)-2-(4-acetylphenoxy)-propionic esters of the formula (I)

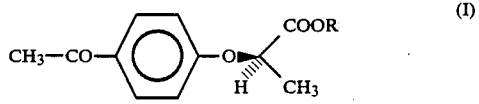

by reacting 4-hydroxyacetophenone with L-lactic acid derivatives of the formula (II)

where, in the formulae indicated,
R is a low-molecular alkyl radical and
A is halogen or a sulfonyloxy group,
which comprises carrying out the reaction in a basic medium at temperatures of not more than 50° C.

Preferably suitable for R are methyl, ethyl, n- and i-propyl and n-, i-, t- and 2-butyl, in particular methyl and ethyl.

Suitable as halogen is preferably chlorine, bromine or iodine; examples of the sulfonyloxy group are methanesulfonyloxy, trifluoromethanesulfonyloxy, benzenesulfonyloxy and o-, m- and p-toluenesulfonyloxy. Particularly preferred leaving groups A are chlorine, bromine, the methanesulfonyloxy or the p-toluenesulfonyloxy group.

The reaction is preferably carried out in a preferably organic solvent or solvent mixture which is inert under the reaction conditions. Examples of suitable solvents are toluene or xylene in connection with phase-transfer catalysts, such as tetraalkylammonium salts or crown ethers, polyethylene glycol or dipolar-aprotic solvents, such as dimethylformamide, N-methylpyrrolidone, dimethyl sulfoxide, sulfolane or acetonitrile.

Either a weak auxiliary base is added to the reaction mixture, or the 4-hydroxyacetophenone is first converted into the alkali metal salt, alkaline earth metal salt or ammonium salt, before reacting it with compounds of the formula (II). Suitable auxiliary bases are, for example, alkali metal carbonates and alkali metal hydrogen carbonates, for example sodium hydrogen carbonate or potassium hydrogen carbonate, sodium carbonate or potassium carbonate. An addition of 1–10% of cesium carbonate has proved advantageous.

The reaction temperature is preferably 20°–50° C, depending on the solvent used, on the group A and on the auxiliary base. As a function of temperature, solvent, auxiliary base and, in some cases, phase-transfer catalysts, the duration of the reaction is 1–20, preferably 2–12 hours.

PREPARATION EXAMPLES (1) 136 g (1.0 mol) of 4-hydroxyacetophenone are added to a suspension of 138 g (1.0 mol) of potassium carbonate in 1 l of dimethyl sulfoxide, and 122.5 g (1 mol) of L-methyl 2-chloropropionate are added within 30 minutes. After the mixture has been stirred for 6 hours at room temperature, 5 g of ground potassium carbonate are added, and stirring is continued for 6 hours at room temperature.

The mixture is poured into 1.5 l of ice-water and extracted using 300 ml of ether. After the fixture has been dried and the ether phase been evaporated off, D(+)-methyl 2-(4-acetylphenoxy)propionate remains as an amber-colored wax which crystallizes slowly. Yield: 209 g (94% of theory); m.p.: 42°–44° C.; $[\alpha]_D^{23} = +45.2°$ (c=1.00 in CHCl$_3$); the purity as determined by gas chromatography is >98.5%; enantiomeric purity (via chiral HPLC): D(+) 93%, L(−) 7%.

(2a) 77.4 (1 mol) of methanesulfonyl chloride are added to a solution of 124.8 ml (1.1 mol) of S-ethyl lactate (94% ee) in 750 ml of tetrahydrofuran, and 166.4 ml (1.2 mol) of triethylamine are added at 20°–22° C. within 1.5 hours. The mixture is heated up to 60° C. within 2 hours, stirring is continued at this temperature for 2 hours, and the batch is transferred to a mixture of ice and concentrated hydrochloric chloric acid. Extraction with ether, drying and concentrating yields 192.7 g (98% of theory) of L-ethyl 2-methanesulfonyloxypropionate as a viscous oil ($[\alpha]_D^{23} = -52.04$ (c=1.38 in CHCl$_3$)). It can be used as a crude product for the reaction below.

(2b) 98 g (0.5 mol) of L-ethyl 2-methanesulfonyloxypropionate, described under (2a), are stirred in 400 ml of DMSO for 30 minutes at room temperature and for 6 hours at 37° C. with 68 g (0.5 mol) of 4-hydroxyacetophenone and 69.1 g (0.5 mol) of potassium carbonate. The product is poured into a mixture of ice/hydrochloric acid, the mixture is extracted using ether, and the dried extract is concentrated, this giving 113.5 g (96%) of D(+)-ethyl 2-(4-acetylphenoxy)-propionate as a yellow viscous oil; $[\alpha]_D^{23} = +44.15$ (c=1 in CHCl$_3$); purity as GC: 97%; enantiomeric purity (via chiral HPLC): D(+) 95.5%, L(−) 4.5%.

To obtain a high optical yield, it is essential to maintain a reaction temperature of no more than 50° C. As shown in Table 1, an increase in temperature results in noticeable racemization of component II (A=Cl, R=CH₃). Coupled to this racemization is a lower optical purity of ether I (R=CH₃), which was synthesized following Preparation Example (1) at different temperatures (Table II).

Table I

Racemization of S-methyl 2-chloropropionate in DMSO in the presence of molar amounts of potassium carbonate ($\alpha_0$=optical rotation before, $\alpha$=optical rotation after treatment)

| Duration of Effect | Temperature | Racemization $(1 - \alpha/\alpha_0) \cdot 100\%$ |
|---|---|---|
| 4 h | 23° C. | <2%* |
| 4 h | 40° C. | 5% |
| 4 h | 60° C. | 60% |
| 1 h | 110° C. | 100% |

Table II

Optical rotation of compound I (R=CH₃) as a function of the temperature during formation

| Temperature | Optical rotation $[\alpha]_D^{23}$ |
|---|---|
| 23° C. | 45.2° |
| 50° C. | 41.4° |
| 60° C. | 39.8° |

The D(+)-2-(4-acetyl-phenoxy)-propionic esters which are prepared at temperatures of not more than 50° C. can be converted into R(+)-2-(4-hydroxyphenoxy)-propionic esters in a Baeyer-Villiger reaction, while maintaining the optical purity (see, for example, J. Am. Chem. Soc. 72, 878 (1950), J 62/178,543). With halogen-substituted heterocyclic compounds, the latter react to give the active enantiomers of known grass herbicides, such as, for example, haloxyfop-methyl, quizalofop-ethyl, fenoxaprop-ethyl or fluazifop-butyl.

We claim:

1. A process for the preparation of a D(+)-2-(4-acetylphenoxy)-propionic ester of the formula (I)

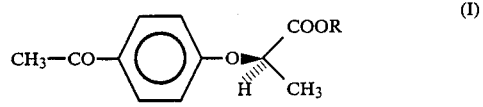

which comprises reacting 4-hydroxyacetophenone with L-lactic acid derivatives of the formula (II),

where, in the formulae (I) and (II)
R is a low-molecular alkyl radical and
A is halogen or a sulfonyloxy group, in a basic medium at temperatures of not more than 50° C.

2. The process as claimed in claim 1, wherein the reaction is carried out at 20° to 50° C.

3. The process as claimed in claim 1, wherein the reaction is carried out in an organic solvent or solvent mixture which is inert under the reaction conditions.

4. The process as claimed in claim 1, wherein an alkali metal carbonate or an alkali metal hydrogen carbonate is employed as auxiliary base.

5. The process as claimed in claim 1, wherein is chlorine, bromine, iodine, methanesulfonyloxy, trifluoromethanesulfonyloxy, benzenesulfonyloxy or toluenesulfonyloxy.

6. The process as claimed in claim 1, wherein R is alkyl having 1 to 4 carbon atoms.

7. The process as claimed in claim 1, wherein the reaction is carried out over 1 to 20 hours.

8. The process as claimed in claim 3, wherein an alkali metal carbonate or an alkali metal hydrogen carbonate is employed as auxiliary base.

9. The process as claimed in claim 3, which comprises carrying out the reaction at a temperature of 20° to 50° C.

10. The process as claimed in claim 4, wherein the reaction temperature is 20° to 50° C.

11. The process as claimed in claim 5, wherein the reaction temperature is 20° to 50° C.

12. The process as claimed in claim 11, wherein the reaction is carried out in an inert organic solvent.

13. The process as claimed in claim 12, wherein an alkali metal carbonate or an alkali hydrogen carbonate is employed as auxiliary base.

* * * * *